United States Patent [19]
Baaten et al.

[11] Patent Number: 5,570,770
[45] Date of Patent: Nov. 5, 1996

[54] APPARATUS, IN PARTICULAR AN X-RAY EXAMINATION APPARATUS, WITH ARRANGEMENT FOR COLLISION PROTECTION

[75] Inventors: Wilhelmus H. Baaten; Wilhelmus J. P. Habraken, both of Eindhoven, Netherlands

[73] Assignee: U.S. Philips Corporation, New York, N.Y.

[21] Appl. No.: 531,267

[22] Filed: Sep. 20, 1995

Related U.S. Application Data

[63] Continuation of Ser. No. 117,904, Sep. 7, 1993, abandoned.

[30]     Foreign Application Priority Data

Sep. 14, 1992 [EP] European Pat. Off. .............. 92202801
Apr. 21, 1993 [EP] European Pat. Off. .............. 93201167

[51] Int. Cl.$^6$ .................................................. F16D 65/34
[52] U.S. Cl. ........................ 192/147; 192/129 A; 477/186
[58] Field of Search ................................. 192/144, 147, 192/129 R, 129 A; 477/184, 185, 186

[56] References Cited

U.S. PATENT DOCUMENTS

| | | | |
|---|---|---|---|
| 4,048,886 | 9/1979 | Zettler | 192/144 X |
| 4,161,649 | 7/1979 | Klos et al. | 192/144 X |
| 4,233,919 | 11/1980 | Takahashi et al. | 192/129 A X |
| 4,402,350 | 9/1983 | Ehret et al. | 141/94 |
| 4,412,162 | 10/1983 | Kitamura | 318/563 |
| 4,578,757 | 3/1986 | Stark | 364/461 |
| 4,888,541 | 12/1989 | Russell | 318/696 |

FOREIGN PATENT DOCUMENTS

| | | | |
|---|---|---|---|
| 0087198 | 11/1987 | European Pat. Off. . | |
| 0059541 | 9/1992 | European Pat. Off. . | |
| 2903702 | 10/1979 | Germany | 192/129 A |
| 147801 | 4/1981 | Germany | 192/129 A |

*Primary Examiner*—Andrea L. Pitts
*Attorney, Agent, or Firm*—Jack D. Slobod

[57]         ABSTRACT

An arrangement for collision prevention is provided for an apparatus, in particular an x-ray examination apparatus, having components that can be moved by drive means. A collision is detected by way of detecting the speed of a relevant moving part and detecting the current and/or power supply to the drive means. Reference values for current and/or power supply at normal operation in dependence of the speed acquired by moving components are provided from a memory means and actually required current and/or power supplies are compared to said reference values. In addition, actual positions of components are detected and compared to computed expected positions of said components. A collision is detected when the required current and/or power supply exceeds a relevant reference value and the detected actual position deviates from the corresponding calculated expected position. As a consequence of a collision being detected, the moving component involved in a collision is detached from the drive means so as to avoid damage or injury as a cause of the collision. Apart from x-ray examination apparatus, also industrial robots which operate in circumstances where person may approach the apparatus to within the reach of moveable components are preferably fitted with an arrangement for collision protection as described above.

20 Claims, 1 Drawing Sheet

APPARATUS, IN PARTICULAR AN X-RAY EXAMINATION APPARATUS, WITH ARRANGEMENT FOR COLLISION PROTECTION

This is a continuation of application Ser. No. 08/117,904, filed Sep. 7, 1993 now abandoned.

BACKGROUND OF THE INVENTION

1. Field of the Invention

The invention pertains to an apparatus, comprising drive means for moving components of said apparatus and further comprising an arrangement for collision protection.

2. Description of the Related Art

An apparatus of said kind is described in the European Patent EP 0 087 198 which corresponds substantially to U.S. Pat. No. 4,578,757.

In the cited reference an x-ray examination apparatus is described that comprises an arrangement for collision protection based on calculation of distances between mutually moveable components or bodies and comparing said distances with safety distances. A collision is considered imminent in the known x-ray examination apparatus when a distance between components of the x-ray apparatus becomes smaller than a predetermined safety distance. Collision protection is achieved in the known x-ray examination apparatus in that movement of said x-ray examination apparatus is terminated when a relevant distance becomes smaller than the safety distance. The arrangement for collision protection as described in the cited reference aims at preventing collisions between components of the known x-ray examination apparatus. Therefore, a patient to be examined by way of a known x-ray apparatus is protected only from experiencing collision with a component of said x-ray examination apparatus when there are provided sufficiently large safety distances from a patient table that is a component of the x-ray apparatus. As a consequence, in the x-ray examination apparatus as described in the cited reference, required patient safety prohibits that the distance between a patient that is to be examined and components of the x-ray apparatus, in particular an x-ray image intensifier, can become arbitrarily small. Hence, spatial resolution of an x-ray image produced by the x-ray image intensifier is compromised by the requirement that an input screen of the x-ray image intensifier should be kept at least a safe distance away from the patient.

It is inter alia an object of the invention to provide an apparatus, such as an x-ray examination apparatus or an industrial robot, comprising an arrangement for collision protection allowing arbitrarily close approach of components of said apparatus, mutually, or of any of such components with a patient that is to be examined, or a person being within a reach of a component of the apparatus.

This is achieved in that such an apparatus, in accordance with the invention is characterized in that the arrangement for collision protection comprises power and/or current measuring means for determining (a) value(s) of power and/or current supplied to the drive means, and comparison means for comparing said determined value(s) of power and/or current supplied to drive means with (a) reference value(s) for said power and/or current supplied and for generating a first drive-disengaging signal for controlling disengaging a relevant component from the drive means.

For the alternative motions of components of an apparatus in accordance with the invention, the power supply required by the drive means under normal circumstances can be measured and thus reference values for the required power supply are known. Should a collision occur of any component of the x-ray apparatus with another object, e.g. with another component of the x-ray apparatus or with a patient that is to be examined, then the motion of the colliding component meets additional resistance and therefore the power supply required by the drive means would increase beyond said reference value. Detection of the required power supply, and subsequently comparing with a relevant reference value provides for generating a first drive-disengaging signal for interrupting the motion of the colliding component, and thus preventing the collision to cause damage or injury.

A preferred embodiment of an apparatus in accordance with the invention is characterized in that the arrangement for collision protection comprises current measuring means for measuring current supplied to the drive means, and current comparison means for comparing (a) measured value(s) of current supplied to drive means with (a) relevant reference value(s) for said current supplied and for generating a first drive-disengaging signal for controlling disengaging a relevant component from the drive means.

Because the drive means is operated at a fixed, or at least at a known, voltage, power supplied to the drive means is conveniently determined by measuring current supplied to the drive means. For the alternative motions of components of the apparatus in accordance with the invention, the current supply required by the drive means under normal circumstances can be measured and thus reference values for the required power supply can be determined and thus reference values for the required current supply are provided. Should a collision occur of any component of the apparatus with another object e.g. with another component of the apparatus, or in case of an x-ray examination apparatus with a patient that is to be examined, then the motion of the colliding component meets additional resistance and therefore the current supplied to the drive means would increase beyond said reference value. Measurement of the current supplied, and subsequently comparing with a relevant reference value provides for generating a first drive-disengaging signal for interrupting the motion of the colliding component, and thus preventing the collision to cause damage or injury.

A further preferred embodiment of an apparatus in accordance with the invention is characterized in that the arrangement for collision protection comprises a memory means for storing said reference value(s).

Reference values for current and/or power supply to drive means of the apparatus being fixed, a particularly simple way of supplying said reference values to the comparison means is to provide a memory means in which reference values can be stored and from which said reference values are supplied to the comparison means. Notably, when current supply to the drive means is compared with a relevant current reference value, the comparison means is formed by a current comparator.

A further preferred embodiment of an apparatus in accordance with the invention is characterized in that the arrangement for collision protection comprises position detection means for detecting a position of a component of the apparatus, and also comprises computing means for calculating an expected position of said component, and further comprises position comparison means for determining a difference between said detected position and said expected position and for generating a second drive-disengaging signal for controlling disengaging a relevant component from the drive means.

By comparing the actual position of a component of the apparatus to the expected position of said component, it is accurately determined if the motion of said component has been obstructed. Collision protection is achieved in that a disengaging signal is generated when the actual position deviates from the expected position in excess of a predetermined threshold value and when also the current and/or power supplied to the drive means exceeds a relevant reference value.

A further preferred embodiment of an apparatus in accordance with the invention is characterized in that the arrangement for collision protection comprises a signal processing means whereto the first and second drive-disengaging signals are supplied and said signal processing means being arranged generate a third drive-disengaging signal for controlling disengaging a relevant component from the drive means, in dependence of the first and second drive-disengaging signals.

A further refined way of detecting obstruction of a component of the apparatus consists of combinedly comparing current and/or power supply to the drive means to a reference value and comparing the detected position of said component to a corresponding expected position. Employing both current and/or power comparison and position comparison, which yield a first drive-disengaging signal and a second drive-disengaging signal, respectively, leads to reliable detection of obstruction, and hence a collision being imminent. If both first and second drive-disengaging signals indicate a collision being imminent, then a third drive disengaging signal is supplied for disengaging the drive means.

A further preferred embodiment of an apparatus in accordance with the invention, also comprising a brake, is characterized in that the arrangement for collision protection comprises brake-engaging means, and a signal processing means arranged to receive relevant drive-disengaging signal(s) and for supplying a brake-engaging signal to said brake engaging means for engaging said brake, after a predetermined period of time after receipt of said drive-disengaging signal(s).

Components of an apparatus which is balanced, are moveable without substantial effort. When a component of an apparatus in accordance with the invention and which is also balanced, is undesiredly obstructed by another component of the apparatus, or with a person within the reach of a component of the apparatus, or with a patient to be examined in the case where the apparatus is an x-ray examination apparatus, a component involved in obstruction is disengaged from the drive means by the arrangement for collision protection and by the recoil following the obstruction, the component involved in obstruction moves in a direction opposite to its direction of motion prior to the obstruction. After a predetermined period of time after generating the disengaging signal for disengaging a component involved in obstruction from the drive means, a brake-engaging signal is generated for engaging a brake, so as to stop a relevant components of the (x-ray examination) apparatus in such a position that neither a patient of another component is obstructed.

A further preferred embodiment of an apparatus in accordance with the invention is characterized in that the arrangement for collision protection comprises a speed detection means for detecting a speed of a moving component and supplying a selection signal to the memory means, for selecting a reference value in correspondence with a detected speed.

In particular when the apparatus is an x-ray examination apparatus, in various stages of an examination procedure, components of the x-ray apparatus are moved with different speeds. The required current and/or power supply is dependent on the speed with which relevant components are moved. By the speed detection means selection signals are supplied to the memory means for selecting appropriate reference values for the current and/or power supply in correspondence with the speed of moving components of the x-ray apparatus.

An apparatus comprising drive means for moving components of said apparatus and further comprising an arrangement for collision protection is characterized in that the arrangement for collision protection comprises means for determining actual values of differences between current and/or power supplies at consecutive instants to the drive means, and difference comparison means being arranged to compare (a) value(s) of (a) difference(s) between current and/or power supplied to drive means with (a) predetermined reference value(s) for said differences between current and/or power supplied and for generating a difference-excess signal for controlling disengaging a relevant component from the drive means.

Should a collision occur of any component of the apparatus with another object e.g. with another component of the apparatus, or with a person within the reach of a component of the apparatus, or in the case where the apparatus is an x-ray examination apparatus, with a patient that is to be examined, then the motion of the colliding component meets additional resistance, and therefore the rate of increase of current and/or power supply required by the drive means would increase beyond said reference value. Detection of the rate of increase of required current and/or power supply, and subsequently comparing with a relevant reference value provides for generating a signal for interrupting the motion of the colliding component, and thus avoiding the collision to cause damage or injury.

An industrial robot, e.g. for welding or for displacing parts, or an automatic manipulator, often comprises moveable components being driven by drive means. Such industrial robots are employed in circumstances where persons are within the reach of one or more of said moveable components. Therefore, providing an arrangement is called for to improve safety and to avoid malfunctioning of the industrial robot. Preferably, an industrial robot in accordance with the invention comprises an arrangement for collision protection comprising current and/or power measuring means for determining (a) value(s) of current and/or power supplied to the drive means, and comparison means for comparing said determined value(s) of current and/or power supplied to drive means with (a) reference value(s) and for generating a first drive-disengaging signal for controlling disengaging a relevant component from the drive means.

An x-ray examination apparatus often comprises moveable parts which are driven by drive means. When performing a medical examination various parts of the apparatus often are positioned close to a patient that is being examined. For example an x-ray image intensifier is preferably placed almost in contact with the patient to obtain x-ray images with good spatial resolution. In order to achieve safety for the patient and to avoid damage to the x-ray apparatus owing to a collision of parts, an x-ray examination apparatus according to the invention comprises an arrangement for collision protection comprising current and/or power measuring means to determine (a) value(s) of current and/or power supplied to the drive means, and comparison means to compare said determined value(s) of current and/or power supplied to the drive means with (a) reference value(s), and to generate or a first drive-disengaging signal for controlling disengaging a relevant component from the drive means.

The various functions which the arrangement for collision protection should execute in an apparatus in accordance with the invention, are preferably performed by a computer suitably programmed for performing said functions.

BRIEF DESCRIPTION OF THE DRAWING

These and other aspects of the invention will become apparent from and elucidated with reference to the embodiments described hereinafter and with reference to the accompanying drawing, wherein.

DETAILED DESCRIPTION OF THE PREFERRED EMBODIMENT

Figure 1:
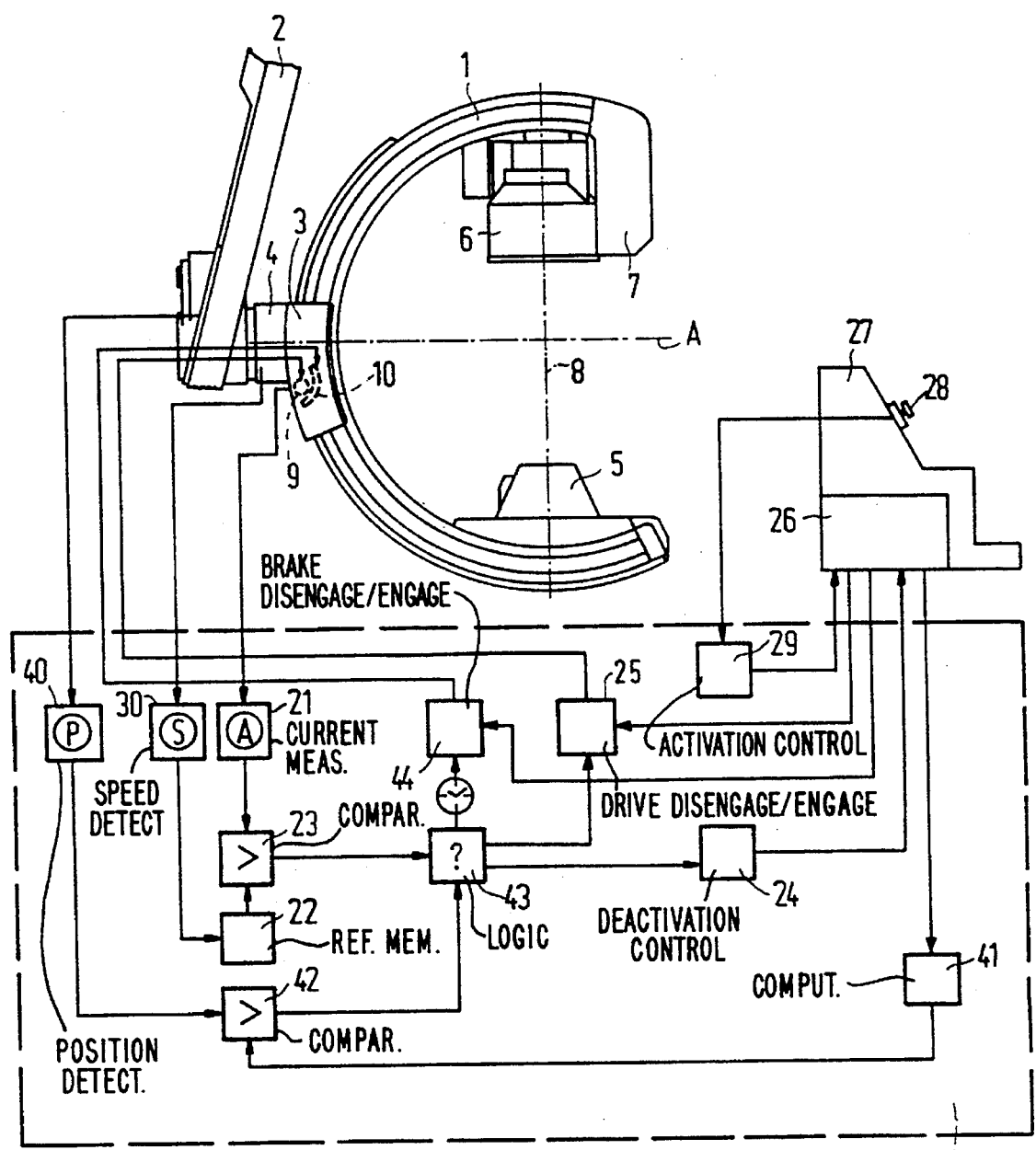
FIG. 1 shows a block scheme of an x-ray examination apparatus comprising an arrangement for collision protection in accordance with the invention.

FIG. 1 shows an x-ray examination apparatus comprising a C-shaped carrier 1 mounted on a predominantly vertical support 2, by means of a sleeve 3 and a bearing 4, and supporting an x-ray source 5, and an x-ray detector 6. The components, e.g. the C-shaped carrier and the x-ray detector, of the x-ray examination apparatus can be moved by way of drive-means 9 incorporated in the x-ray examination apparatus and brakes 10 are provided for maintaining positions of said components. In the embodiment depicted here the x-ray detector is an x-ray image intensifier. The x-ray examination apparatus is balanced in that a counterweight 7 is provided for compensating for a shift in a centre of gravity upon movement of the x-ray image intensifier along the central ray path 8 of the x-ray source of the C-shaped carrier with the x-ray source, the film holder, the frame and the x-ray source. The C-shaped carrier can be moved in the sleeve and the sleeve can be rotated around an axis A, so as to angulate the central ray path. Because the x-ray examination apparatus is balanced, as drive-means there are employed by low-power electric motors that require comparatively weak currents.

An arrangement 50 for collision protection, provided to an x-ray examination apparatus in accordance with the invention will now be discussed. Current supplies required by drive-means incorporated in the x-ray apparatus, for moving different components of the x-ray examination apparatus are measured by current measuring-means 21, e.g. having the form of ammeters. Because the drive-means are operated, usually at a fixed voltage, or at least at a known voltage, the current measuring-means effectively act as determination means for determining power supplied to the drive-means. A reference value for a current supply required by the drive-means for normal operation, i.e. when no obstruction or collision is occurring, are available from a memory-means 22, e.g. having the form of a programmable read-only memory. By way of a comparison-means 23 a current supply required when displacing components of the x-ray examination apparatus is compared to a reference value. Should the current supply required exceed a corresponding reference value then a first drive-disengaging signal is provided to a signal processing means 43 having the form of a logical unit. During motion of a component from a start position to a final position, the required current supply will vary. E.g. a higher current supply is required when a component is set in motion or when a centre of gravity of a component is moved oppositely the direction of gravity. Therefore, during the motion the required current is repeatedly compared to a relevant reference value which is supplied from the memory means 22.

Actual positions of components of the x-ray examination apparatus are detected by position detection-means 40. By way of computation-means 41, being connected to a motion control-part 26, there are calculated expected positions of components of the x-ray examination apparatus. After a command has been supplied from the motion control-part 26 to the drive-means to displace components of the x-ray examination apparatus from a start position to a final position, repeatedly an actual position is detected by position detection-means 40 and an expected position is calculated by computation-means 41. An actual position and a corresponding expected position are compared by a position comparison-means 42. Should a difference, detected by the position comparison-means 42, between an actual position and a corresponding expected position exceed a predetermined value, then a second drive-disengaging signal is provided to the logical unit 43.

Should a movement of a component be obstructed, then a difference between an actual position anti an expected position will exceed a predetermined threshold value and substantially simultaneously the required current for the drive-means will exceed a reference value. In such a situation, substantially simultaneously a first and an second drive-disengaging are supplied to the logical unit 43. Subsequently, by the logical unit 43 a deactivation signal is supplied the deactivation control-means 24 for deactivating the motion control-means, a third drive-disengaging signal is supplied to drive disengaging/engaging-means 25 for disengaging the drive-means and a time-delayed engaging signal is supplied to the brake disengaging/engaging-means 44 for engaging a brake. In its turn by the drive disengaging/engaging-means 25 a relevant component is disengaged from the drive-means and because the x-ray examination apparatus in accordance with the invention is balanced and can therefore be moved without substantial effort, the relevant component moves in reverse direction, by the recoil caused by the occurred obstruction. After some predetermined short period of time, (e.g. ½ second), the brake engaging/disengaging-means 44 that is activated by the time-delayed engaging signal and the brake is engaged, so that the relevant component is stopped in such a position that neither another component or a patient is obstructed. Furthermore, the obstruction not having evolved in a violent impact, damage or injury to a patient to be examined are avoided. Said deactivation signal is supplied to the motion control-part 26 being incorporated in a control desk 27. In addition the deactivation signal for deactivating the motion control-part 26, is supplied to the motion control part 26 of the control desk 27. As a consequence motion control-means 28 e.g. a control button or joy-stick, mounted on the control desk is disengaged from motion control. After said control-means has been released by a person operating the x-ray apparatus, an activation signal is supplied to an activation control circuit-means 29. Subsequently, said activation control circuit-means re-activates the motion control part 26 by way of an activation signal generated by the activation circuit-means 29. After the cause of the obstruction has been removed, the examination procedure can be continued and motion of components of the x-ray apparatus can be performed by way of the control desk.

In various stages of an examination procedure, components of the x-ray apparatus are moved with different speeds, or as an alternative, different speeds for moving components can be selected. The collision preventing arrangement is further refined by providing a speed detection-means 30. The required current supply is dependent on the speed with which relevant components are moved. By the speed detection-means 30 selection signals are supplied to the memory-means 22 for selecting appropriate reference values for the current supply in correspondence with the speed of moving components of the x-ray apparatus.

The invention claimed is:

1. An apparatus comprising a plurality of components, drive means for moving certain of said components of said apparatus in response to power or current supplied to the drive means, and an arrangement for collision protection which comprises measuring means for determining values of the power or current supplied to the drive means, and comparison means for comparing the determined values of power or current supplied to the drive means with corresponding reference values for said power or current supplied and for, in dependance upon a result of said comparing indicating that a relevant one of said moving components has contacted an obstruction, generating a first drive-disengaging signal for controlling disengagement of said relevant one of said moving components from the drive means so as to render said relevant one of said moving components substantially freely moveable with respect to the drive means.

2. An apparatus as claimed in claim 1, wherein the arrangement for collision protection comprises a memory means for storing said reference values.

3. An apparatus as claimed in claim 2, wherein the arrangement for collision protection further comprises a speed detection means for detecting a speed of one of said moving components and supplying a selection signal to the memory means, for selecting a corresponding reference value in dependance upon the detected speed.

4. An apparatus as claimed in claim 2, also comprising a brake, wherein the arrangement for collision protection further comprises brake-engaging means for engaging said brake in response to a brake-engaging signal, and a signal processing means arranged to receive relevant the first drive-disengaging signal and for supplying the brake-engaging signal to said brake engaging means a predetermined period of time after receipt by said signal processing means of said first drive-disengaging signal.

5. An apparatus as claimed in claim 2, wherein the arrangement for collision protection further comprises position detection means for detecting an actual position, and computing means for calculating an expected position, of one of said moving components, and position comparison means for determining a difference between said detected actual position and said computed expected position and for, in dependence upon the determined difference, generating a second drive-disengaging signal for controlling disengagement of a relevant one of said moving components from the drive means.

6. An apparatus as claimed in claim 5, wherein the arrangement for collision protection further comprises a signal processing means to which the first and second drive-disengaging signals are supplied and said signal processing means is arranged to generate a third drive-disengaging signal for controlling disengaging a relevant one of said moving components from the drive means, in dependence upon the first and second drive-disengaging signals.

7. An apparatus as claimed in claim 6, also comprising a brake, wherein the arrangement for collision protection further comprises brake-engaging means for engaging said brake in response to a brake-engaging signal, and a signal processing means arranged to receive relevant at least one of the first drive-disengaging signals and for supplying the brake-engaging signal to said brake engaging means a predetermined period of time after receipt by said signal processing means of said at least one of said first and second drive-disengaging signals.

8. An apparatus as claimed in claim 6, wherein the arrangement for collision protection further comprises a speed detection means for detecting a speed of one of said moving components and supplying a selection signal to the memory means, for selecting a corresponding reference value in dependance upon the detected speed.

9. An apparatus as claimed in claim 5, also comprising a brake, wherein the arrangement for collision protection further comprises brake-engaging means for engaging said brake in response to a brake-engaging signal, and a signal processing means arranged to receive relevant at least one of the first drive-disengaging signals and for supplying the brake-engaging signal to said brake engaging means a predetermined period of time after receipt by said signal processing means of said at least one of said first and second drive-disengaging signals.

10. An apparatus as claimed in claim 1, also comprising a brake, wherein the arrangement for collision protection further comprises brake-engaging means for engaging said brake in response to a brake-engaging signal, and a signal processing means arranged to receive relevant the first drive-disengaging signal and for supplying the brake-engaging signal to said brake engaging means a predetermined period of time after receipt by said signal processing means of said first drive-disengaging signal.

11. An apparatus as claimed in claim 1, wherein said comparing and first drive-disengaging signal generating means are comprised by a computer.

12. An apparatus as claimed in claim 1, said apparatus being an industrial robot.

13. An apparatus as claimed in claim 1, said apparatus being an x-ray examination apparatus.

14. An apparatus comprising a plurality of components, drive means for moving certain of said components of said apparatus in response to power or current supplied to the drive means and an arrangement for collision protection which comprises means for determining actual values of differences between the current or power supplied to the drive means at consecutive instants, and difference comparison means for comparing the determined actual values of the differences between current or power supplied to the drive means at consecutive instants with predetermined corresponding reference values for said differences and for, in dependance upon a result of said comparing indicating that a relevant one of said moving components has contacted an obstruction, generating a difference-excess signal for controlling disengagement of the relevant one of said moving components from the drive means so as to render said relevant one of said moving components substantially freely moveable with respect to the drive means.

15. An apparatus comprising a plurality of components, drive means for moving certain of said components of said apparatus in response to power or current supplied to the drive means, and an arrangement for collision protection which comprises measuring means for determining values of the power or current supplied to the drive means, and comparison means for comparing the determined values of power or current supplied to the drive means with corresponding reference values for said power or current supplied and for, in dependance upon a result of said comparing, generating a first drive-disengaging signal for controlling disengagement of a relevant one of said moving components from the drive means, wherein the arrangement for collision protection further comprises position detection means for detecting an actual position, and computing means for calculating an expected position, of one of said moving components, and position comparison means for determining a difference between said detected actual position and said computed expected position and for, in dependence upon the determined difference, generating a second drive-disengaging signal for controlling disengagement of a relevant one of said moving components from the drive means.

16. An apparatus as claimed in claim 15, wherein the arrangement for collision protection further comprises a signal processing means to which the first and second drive-disengaging signals are supplied and said signal processing means is arranged to generate a third drive-disengaging signal for controlling disengaging a relevant one of said moving components from the drive means, in dependence upon the first and second drive-disengaging signals.

17. An apparatus as claimed in claim 16, also comprising a brake, wherein the arrangement for collision protection further comprises brake-engaging means for engaging said brake in response to a brake-engaging signal, and a signal processing means arranged to receive relevant at least one of the first drive-disengaging signals and for supplying the brake-engaging signal to said brake engaging means a predetermined period of time after receipt by said signal processing means of said at least one of said first and second drive-disengaging signals.

18. An apparatus as claimed in claim 6, wherein the arrangement for collision protection further comprises a speed detection means for detecting a speed of one of said moving components and supplying a selection signal to the memory means, for selecting a corresponding reference value in dependance upon the detected speed.

19. An apparatus as claimed in claim 15, also comprising a brake, wherein the arrangement for collision protection further comprises brake-engaging means for engaging said brake in response to a brake-engaging signal, and a signal processing means arranged to receive relevant at least one of the first drive-disengaging signals and for supplying the brake-engaging signal to said brake engaging means a predetermined period of time after receipt by said signal processing means of said at least one of said first and second drive-disengaging signals.

20. An apparatus as claimed in claim 15, wherein the arrangement for collision protection further comprises a speed detection means for detecting a speed of one of said moving components and supplying a selection signal to the memory means, for selecting a corresponding reference value in dependance upon the detected speed.

* * * * *